United States Patent [19]
Fischer et al.

[11] Patent Number: 6,034,222
[45] Date of Patent: Mar. 7, 2000

[54] METHOD FOR THE SEPARATION OF RECOMBINANT PRO-FACTOR IX FROM RECOMBINANT FACTOR IX

[75] Inventors: Bernhard Fischer, Vienna; Artur Mitterer, Orth/Donau; Friedrich Dorner; Johann Eibl, both of Vienna, all of Austria

[73] Assignee: Bio-Products & Bio-Engineering A.G., Vienna, Austria

[21] Appl. No.: 08/538,893

[22] Filed: Oct. 4, 1995

[30] Foreign Application Priority Data

Oct. 4, 1994 [DE] Germany .............................. 44 35 520

[51] Int. Cl.$^7$ .............................. A61K 35/14; A23J 1/00
[52] U.S. Cl. .......................... 530/381; 530/412; 530/416
[58] Field of Search .................................. 530/412, 413, 530/416, 381

[56] References Cited

U.S. PATENT DOCUMENTS

| | | | |
|---|---|---|---|
| 4,885,277 | 12/1989 | Nawroth et al. | ............................ 514/15 |
| 5,171,569 | 12/1992 | Anson et al. | ......................... 424/94.64 |

FOREIGN PATENT DOCUMENTS

| | | |
|---|---|---|
| 0317376B1 | 5/1989 | European Pat. Off. . |
| 0363126B1 | 4/1990 | European Pat. Off. . |
| 0430930B1 | 6/1991 | European Pat. Off. . |
| 0229026B1 | 11/1995 | European Pat. Off. . |

OTHER PUBLICATIONS

Liebman et al. (1985) Proc. Natl. Acad. Sci. USA 82, pp. 3879–3883.
Harris et al. (eds.) Protein purification methods (1989), pp. 56–66 and 202–210.
Bristol et al. (1993) J. Biol. Chem. 268, pp. 7577–7584.
Parmacia catalog (1993), pp. 328–332, 343, 344.
Tulinsky, "The Structures of Domains of Blood Proteins", Thrombosis and Hemostasis, vol. 66, No. 1, pp. 16–31 (1991).
Furie et al., "The Molecular Basis of Blood Coagulation", Cell, vol. 53, pp. 505–518, (1988).
Anderson et al., "Purification and Characterization Human Factor IX", Thrombosis Research, vol. 7, pp. 451–459, (1975).
Busby et al., "Expression of Active Human Factor IX in Transfected Cells", Nature, vol. 316 pp. 271–273, (1985).
Rees et al., "The Role of β–Hydroxyaspartate and Adjacent Carboxylate Residues in the First EGF Domain of Human Factor IX", The EMBO Journal, vol. 7, No. 7, pp. 2053–2061, (1988).
Meulien et al., "Increased biological Activity of a Recombinant Factor IX Variant Carrying Alanine at Position +1", Protein Engineering, vol. 3, No. 7, pp. 629–633, (1990).
Suttie, "Current Advances in Vitamin K Research", Proceedings of the Seventeenth Steenbock Symposium, pp. 199–207, (1987).

Falkner et al., "High level Expression of Active Human Prothrombin in a Vaccina Virus Expression System", Thrombosis and Hemostasis, vol. 68, No. 2, pp. 119–124, (1992).

Barrett et al., "Large–Scale Production and Purification of a Vaccinia Recombinant–Derived HIV–1 gp 160 and Analysis of Its Immunogenicity", AIDS Res. and Human Retroviruses, vol. 5, No. 2, pp. 159–171, (1989).

Putney et al., "Large–Scale Production, Purification, and Immunologic Analysis of a Vaccinia Recombinant Derived HIV–1 gp 160", AIDS Vaccine Research and Clinical Trials, pp. 219–277, (1990).

Laemmli, "Cleavage of Structural Proteins During the Assembly of the Head of Bacteriophage T4", Nature, vol. 227, pp. 680–685, (1970).

Bradford, "A Rapid and Sensitive Method for the Quantitation of Microgram Quantities of Protein Utilizing the Principle of Protein–Dye Binding", Analytical Biochemistry, vol. 72, pp. 248–254, (1976).

Balland et al., "Characterisation of Two Differently Processed Forms of Human Recombinant Factor IX Synth. in CHO Cells Trans. With a Polycistronic Vector", Eur. J. Biochem., vol. 172, pp. 565–572, (1988).

Kaufman et al., "Expression, Purification, and Characterization of Recombinant γ–Carboxylated Factor IX Synthesized in Chinese Hamster Ovary Cells", J. Biol. Chem. vol. 261, No. 21, pp. 9622–9628, (1986).

Wasley et al., "PACE/Furin Can Process the Vitamin K–Dependent Pro–Factor IX Precursor Within the Secretory Pathway", J. Biol. Chem., vol. 268, No. 12, pp. 8458–8465, (1993).

*Primary Examiner*—Ponnathapura Achutamurthy
*Assistant Examiner*—Elizabeth Slobodyansky
*Attorney, Agent, or Firm*—Baker & Botts, L.L.P.; Ronald B. Hildreth

[57] ABSTRACT

A method for separation of recombinant pro-Factor IX from recombinant Factor IX by a chromatographic method is described. According to a preferred embodiment, the mixture of both proteins is bound to an ion exchanger and pro-Factor IX and Factor IX are eluted separately from each other by buffer solutions with different salt concentrations and/or pH values.

According to the method of the invention, pro-Factor IX and Factor IX are obtainable in highly pure form and free from the other factor respectively.

8 Claims, 4 Drawing Sheets

METHOD FOR THE SEPARATION OF RECOMBINANT PRO-FACTOR IX FROM RECOMBINANT FACTOR IX

The invention relates to a method for the separation of recombinant pro-Factor IX from recombinant Factor IX.

BACKGROUND OF THE INVENTION

The conversion of fluid blood to a blood clot, a gelatinous mass which causes the sealing of injured blood vessels by clot formation, occurs in blood clotting. Thereby, the conversion of the soluble fibrinogen present in plasma to the fibrous, gelatinous coagulation material, fibrin, occurs in a multi-step process (the so-called blood coagulation cascade) in which at least 15 different blood coagulation factors, which are characterized with roman numerals, are involved, each of which, when activated, activates the next respective inactive step.

Among the blood factors, calcium ions (Factor IV), fibrinogen (Factor I) and prothrombin (Factor II) continuously circulate in the blood, others are activated by tissue injury (Factor III) or contact with collagen or phospholipids from thrombocytes (Factor XII). Several serine proteases, such as kallikrein, thrombin and the activated Factors VII, IX, X and XI, are found among the remaining blood clotting factors.

In the presence of von Willebrand Factor (a component of clotting Factor VIII), thrombocytes cling to the collagen of injured connective tissue by adhesion. They change their form and develop protrusions, and in addition to this, their outer membrane facilitates the adhesion of further thrombocytes. Thereafter, various substances are released from their granula, whereby vessel constriction as well as accumulation and activation of other factors of plasmic blood clotting are brought about.

In hemophilia (bleeder's disease), blood clotting is disturbed by a lack of certain plasmic blood clotting factors. In hemophilia A, the tendency to bleed is caused by a lack of Factor VIII; in hemophilia B, a lack of Factor IX. Thereby, either the synthesis of the Factor protein can be decreased or a defective molecule with reduced activity is formed. The treatment of hemophilia occurs by replacement of the missing clotting factor by factor concentrates from blood conserves.

Several of the proteins involved in human blood clotting possess an affinity for metal ions, such as $Ca^{2+}$ ions. This affinity is absolutely essential for the function of the clotting factors. The binding occurs through glutamic acid residues; thereby, several glutamic acid residues (Glu) of the N-terminal Gla region of various clotting factors are converted to 4-carboxy-L-glutamic acid (Gla) in a vitamin K dependent reaction (see A. Tulinsky, Thromb. Haemost. 66 (1991) 16–31). These Gla residues then bring about the binding of divalent metal ions (see B. Furie and B. C. Furie, Cell 53 (1988) 508–518).

In the biosynthesis of vitamin K dependent clotting factors in humans, a precursor molecule is first formed whose N-terminus has an additional pre-pro-sequence.

The pre-pro-sequence represents a signal sequence which causes the oriented transport of the protein in the cell. This pre-sequence is cleaved in secretion of the protein from the cell. The pro-sequence consists of about 15 to 18 amino acids and serves as a recognition sequence in the conversion of the glutamic acid residues to 4-carboxy-L-glutamic acid. After successful carboxylation, the pro-sequence is also cleaved. If the pro-sequence is not cleaved or only incompletely cleaved, only low activity clotting factors result. Human Factor IX has a molecular weight of about 55,000 Dalton. Its pro-sequence consists of 18 amino acids, whereby the molecular weight is increased by about 2000 Dalton. In the purification of Factor IX from plasma, active Factor IX is almost exclusively obtained. The purification of Factor IX from plasma is, however, very difficult because Factor IX is only present in low concentration in plasma (5 μg/ml; see L. O. Andersson, Thrombosis Research 7 (1975) 451–459).

Therefore, it is desirable to have recombinant Factor IX made available for the treatment of patients affected with hemophilia.

The DNA sequence of Factor IX used for expression also comprises the pre-pro-sequences. It is expected from the expressing cell systems that they quantitatively cleave these sequences for complete processing of Factor IX and secrete a physiologically active clotting factor. However, in the case of Factor IX, it has been determined that the inherent potential of transformed cells for cleaving the pro-sequence is not sufficient. Therefore, various efforts for the production of recombinant Factor IX have led to products with only low activity (R. J. Kaufman et al., J. Biol. Chem. 261 (1986) 9622–9628; S. Busby et al., Nature 316 (1985) 217–273; D. J. G. Rees et al., EMBO J. 7 (1988) 2053–2061). This can be traced back to an incomplete cleavage of the pro-sequence (P. Meulien et al., Prot. Engineer. 3 (1990) 629–633) because a mixture of recombinantly produced pro-Factor IX and Factor IX is present in cell supernatants.

Up to now, an improvement in the recovery of recombinant, physiologically active Factor IX could only be achieved through genetic manipulation of the pro-sequence. It has thus been attempted to couple the pro-sequence of Factor VII to the DNA sequence of Factor IX in order to obtain a more effective cleavage of the pro-sequence (K. Berkner et al., Current Advances in Vitamin K Research, Elsevier Science Publishing Co., Inc. (1988) 199–207). P. Meulien et al., Prot. Engineer. 3 (1990) 629–633) examined the influence of mutations in the region of the pro-peptide cleavage site of Factor IX. They determined that the yield of active Factor IX can be distinctly increased by introduction of a point mutation in position +1 (alanine versus tyrosine); in comparison with wild-type Factor IX, which demonstrates a specific activity of 45–55% after purification over a DEAE-Sepherodex® column and stepwise elution with 0.3 M NaCl in the physiological pH range, a specific activity of 85 to 100% was found for the mutated Factor IX.

SUMMARY OF THE INVENTION

The object of the present invention is to make a method available with which recombinant inactive pro-Factor IX can be separated from recombinant active Factor IX in an efficient, simple and safe manner.

This object is solved with the subject matter of the present invention.

Subject matter of the present invention is a method for the chromatographic separation of recombinant pro-Factor IX from recombinant Factor IX. This chromatographic separation can occur because the mixture of the two proteins binds to an ion exchanger and pro-Factor IX and Factor IX are eluted separately from each other by buffer solutions with different salt concentrations and/or pH values. The chromatographic separation can, however, also occur because a chromatographic column is used on which one of the proteins is quantitatively bound and the other protein is collected in the eluate. The bound protein can then be eluted by alteration of the buffer composition.

The techniques described below can be employed in a variety of combinations that will become apparent to the skilled artisan in view of the teachings of this specification.

Preferred embodiments of the present invention include methods where an anion exchanger, such as QAE, BEAE or TMAE, is used as the ion exchanger. The elution of pro-Factor IX and Factor IX can occur by increasing the salt gradient and/or decreasing the pH gradient. The elution of pro-Factor IX can occur at a lower salt concentration or higher pH value than the elution of Factor IX.

Other methods include having one of the two proteins bound to a chromatography column. The other is contained in the eluate, and the bound protein is subsequently eluted by alteration of the buffer composition. The bound protein can eluted by alteration of the pH value of the buffer solution.

Buffer solutions with pH values between 5.0 and 10.0 can be used as elution buffers. These buffer solutions can comprise a salt of a monovalent cation, and be in a concentration in the range of 10 mM to 1000 mM. The bound protein also can be eluted with buffer solutions which comprise an inorganic or organic salt, preferably NaCl, $MgCl_2$, KSCN or urea, or which comprise a hydrophobic agent, preferably ethylene glycol. The salt concentration for elution of the bound protein can be in the range of 500 mM to 3.5 M, and the hydrophobic agent concentration can be in the range of 0.1 to 50 percent by weight, preferably 0.1 to 10 percent by weight. The pH value of the elution buffer can be below 7.0, preferably below 5.0, or can be above 8.0, preferably above 9.0.

Other purification techniques include the use of an immunoaffinity column has a bound monoclonal or polyclonal antibody which recognizes either the pro-peptide of pro-Factor IX or Factor IX. Additionally, an immunoaffinity column can comprise a bound monoclonal or polyclonal antibody which recognizes the pro-peptide of pro-Factor IX. For example, the pro-Factor IX can be bound to the column and pure Factor IX would then be present in the eluate. The pro-Factor IX would then be eluted from the column by increasing salt concentration, adding agents or altering pH value.

Further subject matter of the present invention is a highly pure recombinant Factor IX, which is free from pro-Factor IX, which is at least 95 percent pure, and preferably 98 percent pure and which is obtainable according to the method of the invention.

In a preferred embodiment, the ratio of Factor IX-antigen to active Factor IX is ≦1.1.

Further subject matter of the present invention is also a highly pure recombinant pro-Factor IX, which is free from Factor IX, which is at least 95 percent pure, and preferably 98 percent pure, and can be therapeutically employed as an antagonist towards Factor IX, or is obtainable according to the method of the invention.

Further subject matter of the present invention is a pharmaceutical composition which is characterized in that it comprises the highly pure Factor IX (at least 95 percent pure, and preferably 98 percent pure, and preferably the ratio of Factor IX antigen to active Factor IX is less than or equal to 1.1) according to the invention in a physiologically acceptable carrier as well as a pharmaceutical composition according to claim 25 which is characterized in that it comprises highly pure pro-Factor IX (at least 95 percent pure, and preferably 98 percent pure) according to the invention in a physiologically acceptable carrier.

The invention further includes using a highly pure recombinant pro-Factor IX as an antagonist of Factor IX. The pro-Factor IX can be used to make a pharmaceutical preparation with an antagonistic effect towards Factor IX.

Recombinant Factor IX was recovered according to customary methods therefor after infection of Vero cells (monkey kidney cells) with vaccinia virus in cell culture. The Vero/vaccinia expression systems and cell culture conditions are described in detail in F. G. Falkner et al., Thrombosis and Haemostasis 68 (1992) 119–124, N. Barrett et al., AIDS Res. 5 (1989) 159–171 and F. Dorner et al., AIDS Vaccine Research and Clinical Trials, Marcel Dekker, Inc. New York (1990). The expression of recombinant Factor IX occurs in synthetic DMEM standard medium (Dulbeccos minimal essential medium). The culture supernatant was separated by centrifugation.

The purification of recombinant Factor IX from cell-free culture medium occured by customary methods, such as are described by L. O. Andersson (loc.cit.). As a result, a mixture of recombinant Factor IX and pro-Factor IX is obtained.

For the method according to the invention, natural and synthetic hydrophilic gels can be used as an ion exchanger. Preferably, gels with strong anion exchange groups are used, for example as a representative of natural gels, QAE (QAE-Sephadex®, a strong basic anion exchanger comprised of dextran gels which are modified by introduction of N,N-diethyl-N-(2-hydroxy-1-propyl)-ammonio-ethyl groups), DEAE (DEAE cellulose, diethylaminoethyl cellulose) or TMAE (TMAE cellulose, triethylammonioethyl cellulose).

However, immunoaffinity chromatography is also suitable for the method according to the invention, whereby antibodies which bind either the pro-peptide of pro-Factor IX or selectively bind Factor IX are immobilized on a suitable matrix. Thereby, monoclonal and polyclonal antibodies are equally suitable.

The elution can occur by means of buffer solutions with different salt concentrations or with different pH values or a combination of both buffer solutions.

Preferably, such elution solutions with different pH values are used which have pH values between 5.0 and 10.0. The elution by means of buffer solutions with different salt concentrations preferably occurs with buffer solutions which comprise a salt of a monovalent cation, particularly such as NaCl. The salt concentration is preferably in the range from 10 to 1000 mM, and especially in the range of 150 to 400 mM.

The elution of the bound protein from the immunoaffinity column by an alteration in the composition of the buffer solution can take place by addition of an inorganic or organic salt, whereby NaCl, $MgCl_2$, KSCN or urea are preferably used, or a hydrophobic agent such as ethylene glycol is added. The salt concentration is preferably in a region of 500 mM to 3.5 M, especially in a region of 1.0 to 3.5 M. The concentration of the agent is preferably in a region of 0.1 to 50% by weight, preferably 0.1 –10% by weight. However, the change of the buffer composition can also occur by changing the pH value of the buffer, whereby a decrease of the pH value to below pH 7.0, preferably below 5.0, or rather, an increase in the pH value to above 8.0, preferably 9.0, is possible.

In the method according to the invention, the elution of pro-Factor IX and Factor IX preferably occurs by an increasing salt gradient and/or a decreasing pH gradient.

Thereby, the elution of pro-Factor IX occurs at lower salt concentrations or higher pH values than the elution of Factor IX.

The ratio of Factor IX-antigen to active Factor IX obtainable according to the method of the invention is preferably ≦1.1.

According to the method of the invention, a recombinant Factor IX, which is free from pro-Factor IX, i.e. which is at least 95%, in particular 98%, pure, can be obtained in an efficient and simple manner. A recombinant pro-Factor IX, which is free from Factor IX, i.e. which is at least 95% and in particular 98% pure, can also be obtained with this method. This pro-Factor IX is therapeutically employed as an antagonist to Factor IX.

For the production of pharmaceutical preparations, the separated, highly pure Factor IX and pro-Factor IX containing fractions are preferably concentrated and used further as a concentrate.

The production of pharmaceutical compositions can occur in a known and customary manner. Preferably, the highly pure products (Factor IX or pro-Factor IX) or their concentrates are mixed with a suitable physiologically acceptable carrier. Preferably, a sodium chloride solution serves as a carrier.

The pharmaceutical compositions can be present in an administrative form customary and common for the treatment of hemophilia; preferably, they are present in the form of a preparation suitable for infusion.

The use of pro-Factor IX is based on its identical binding capacity for calcium ions and phospholipids which is mediated by the identical Gla and EGF regions present in Factor IX as well as in pro-Factor IX. Thereby, the binding of pro-Factor IX competitively inhibits the binding of Factor IX, and therewith, as an antagonist, reduces the physiological effect of Factor IX.

This is of great significance when the blood clotting cascade must be selectively blocked due to a certain medical indication. Aside from the desired effect, conventional anticoagulants such as heparin or coumarin demonstrate strong side effects. Additionally, their short half-life require frequent application. The use of genetically altered blood coagulation factors, for example Factor VII and Factor X, as anticoagulants has been discussed recently. Peptides were described specifically for the inhibition of Factor IX which code for the EGF domain of Factor IX and prevent the binding of Factor IX to the receptors of the endothelial cells (see U.S. Pat. No. 4885277).

Therefore, subject matter of the present invention is also the use of highly pure recombinant pro-Factor IX as a Factor IX antagonist as well as the use of highly pure recombinant pro-Factor IX for the production of a pharmaceutical composition with an antagonistic effect toward Factor IX.

In the following Examples, the invention is more closely illustrated without limiting the invention to the Examples.

Example 1 describes the separation of pro-Factor IX from Factor IX on an ion exchange column by a linear salt gradient. Example 2 describes the separation of pro-Factor IX from Factor IX by a stepwise elution of the anion exchange column. Example 3 describes the separation of pro-Factor IX and Factor IX by pH dependent elution. In Example 4, the separation of pro-Factor IX and Factor IX by immunoaffinity chromatography is described.

DETAILED DESCRIPTION OF PREFERRED EMBODIMENTS

Example 1

Separation of Recombinant Pro-Factor IX from Recombinant Factor IX by Linear Elution Materials:

Column: Mono-Q 5/5 HR, volume 1 ml (Pharmacia)

Instrument: Pharmacia FPLC LCC-500

Buffer A: 50 mM Tris/20 mM citrate, pH 7.4, 150 mM NaCl

Buffer B: 50 mM Tris/20 mM citrate, pH 7.4, 300 mM NaCl

The anion exchanger was regenerated and equilibrated with Buffer A. Subsequently, 5 ml of the mixture of recombinant Factor IX/pro-Factor IX which was produced with the Vero/vaccinia expression system described above was applied to the column with a speed of 1 ml/min. Material not bound to the column is removed by washing with Buffer A with the same flow speed. Then, by mixing buffer A and buffer B, the column was eluted in a 50 ml volume by means of a linear NaCl gradient from 150 mM to 300 mM. Fractions of 2 ml were collected. During the chromatography, the protein absorption was followed in the customary manner at 280 nm. The protein concentration was determined by means of the Bradford method (M. Bradford, Anal. Biochem. 72 (1976) 248–254) and the activity of Factor IX by means of a commercial coagulation test (Factor IX coagulation, Immuno AG). The concentration of Factor IX-antigen was determined by means of ELISA (Diagnostica Stago).

Figure 1A:
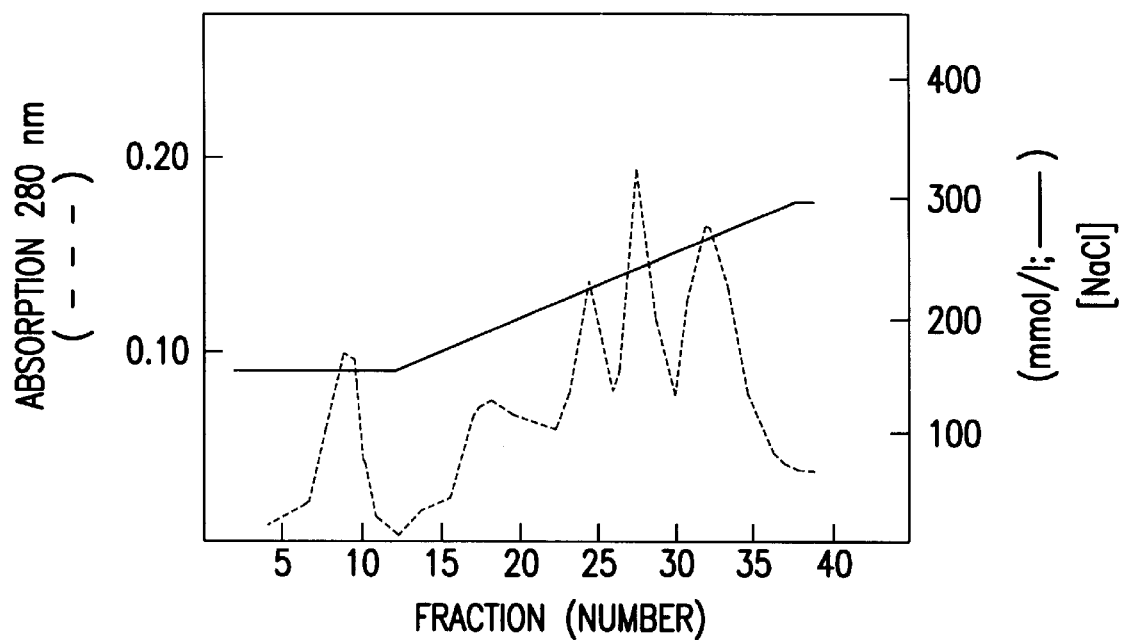
FIG. 1(A and B): a linear chromatography of Factor IX/pro-Factor IX (A: protein absorption; B: antigen concentration, Factor IX clotting activity).
Figure 1B:
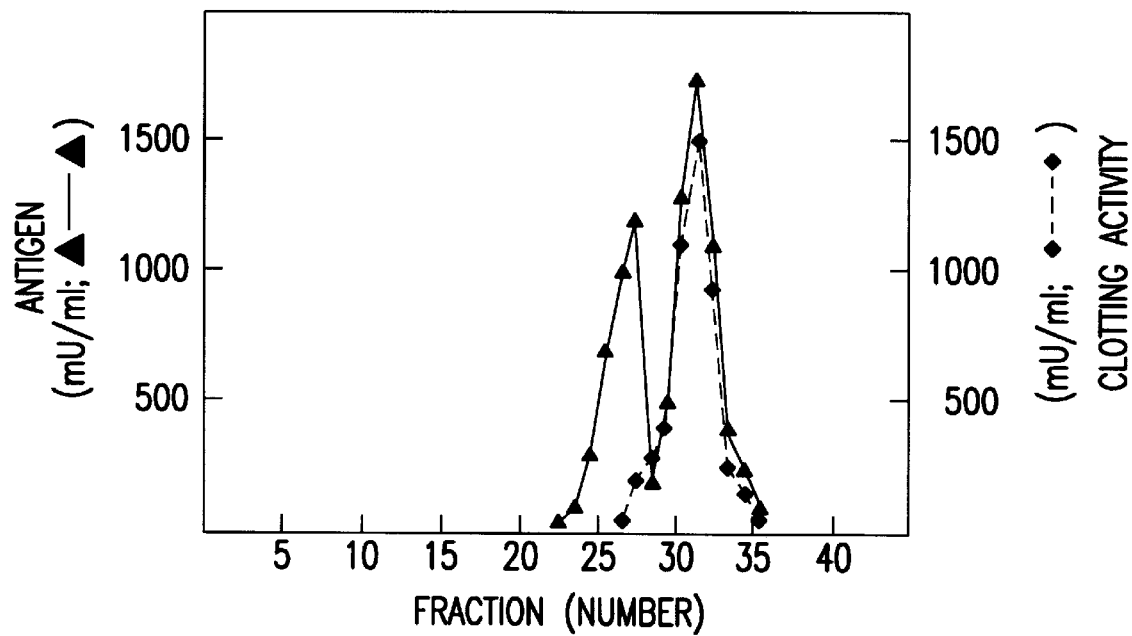
Figure 2:
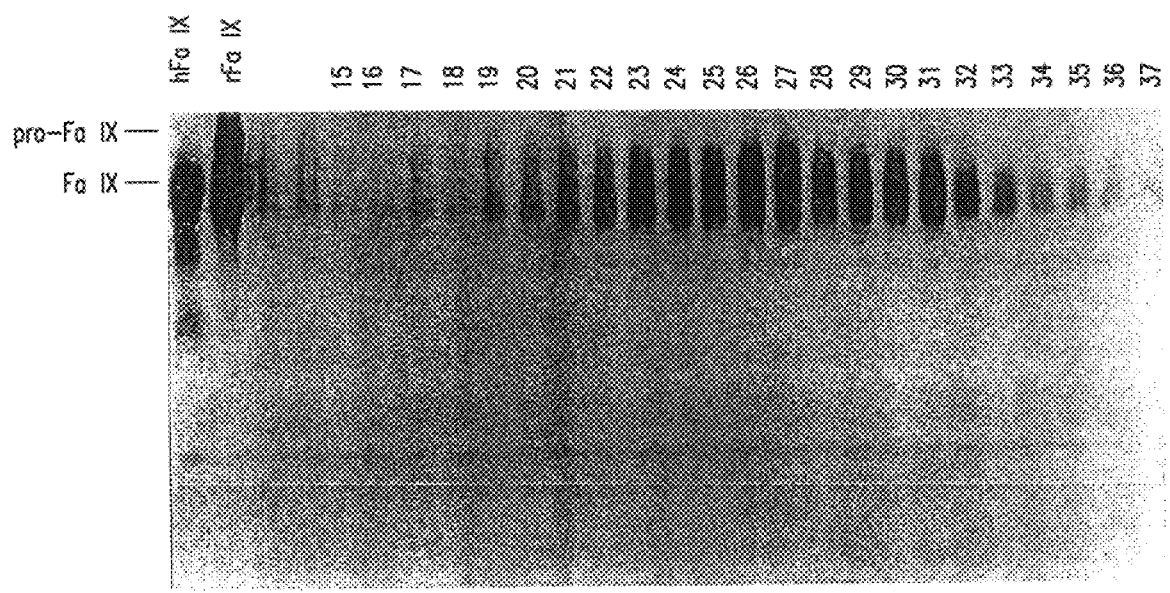
FIG. 2: a denaturing electrophoresis of Factor IX/pro-Factor IX from the purification fractions of the linear chromatography.

FIG. 1 shows the chromatography profile obtained according to Example 1. Thereby, it was established that Factor IX-antigen was eluted from the column in two separate elution ranges (fractions 22 to 28 and fractions 29 to 35). The examination by means of denaturing electrophoresis (U. K. Laemmli, Nature 227 (1970) 680–685) established that the Factor IX-antigen of fractions 22 to 28 has a higher molecular weight of about 2000 over the Factor IX-antigen of fractions 29–35 (FIG. 2). The examination of the clotting profile of the elution fractions established that physiologically active Factor IX was only obtained in the fractions 29 to 35 (Table 1).

TABLE 1

Separation of pro-Factor IX and Factor IX by linear anion exchange chromatography

| Material | Volume (ml) | F IX:Ag (U) | F IX:C (U) | F IX:Ag/F IX:C |
|---|---|---|---|---|
| mixture | | | | |
| pro-F IX/F IX | 5 | 28.0 | 17.0 | 1.7 |
| Fraction 22–28 | 14 | 7.3 | 1.0 | 7.3 |
| Fraction 29–35 | 14 | 10.8 | 9.5 | 1.1 |

Example 2

Separation of Recombinant Pro-Factor IX from Recombinant Factor IX by Stepwise Elution Materials:

Column: Mono-Q 5/5 HR, volume 1 ml (Pharmacia)

Instrument: Pharmacia FPLC LCC-500

Buffer A: 50 mM Tris/20 mM citrate, pH 8.5, 220 mM NaCl

Buffer B: 50 mM Tris/20 mM citrate, pH 8.5, 300 mM NaCl

As in Example 1, a mixture of recombinant pro-Factor IX and Factor IX which was produced with the Vero/vaccinia expression system described above served as starting material.

The ion exchange column was regenerated and equilibrated with Buffer A. Subsequently, 90 ml of the Factor IX/pro-Factor IX mixture was applied to the column with a speed of 1 ml/min. Then, the column was washed with buffer A. Protein bound to the column was then eluted by elution with buffer B. Fractions of 2 ml were collected. The protein and/or Factor IX-antigen concentration as well as the clotting tests were performed as described in Example 1.

Figure 3:
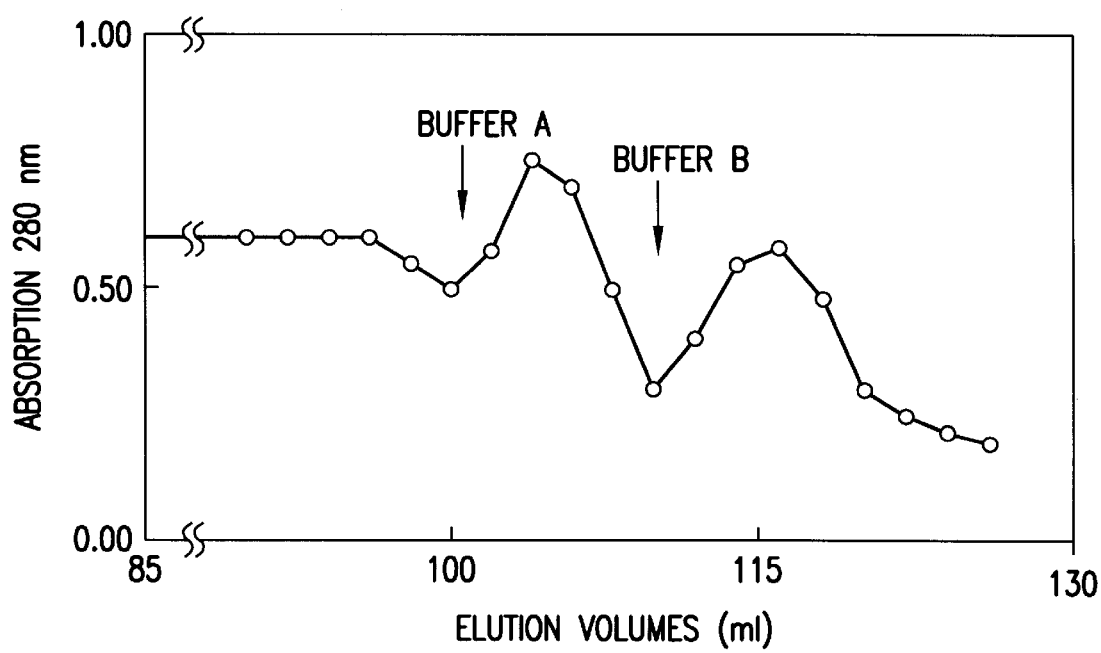
FIG. 3: a stepwise chromatography of Factor IX/pro-Factor IX
Figure 4:
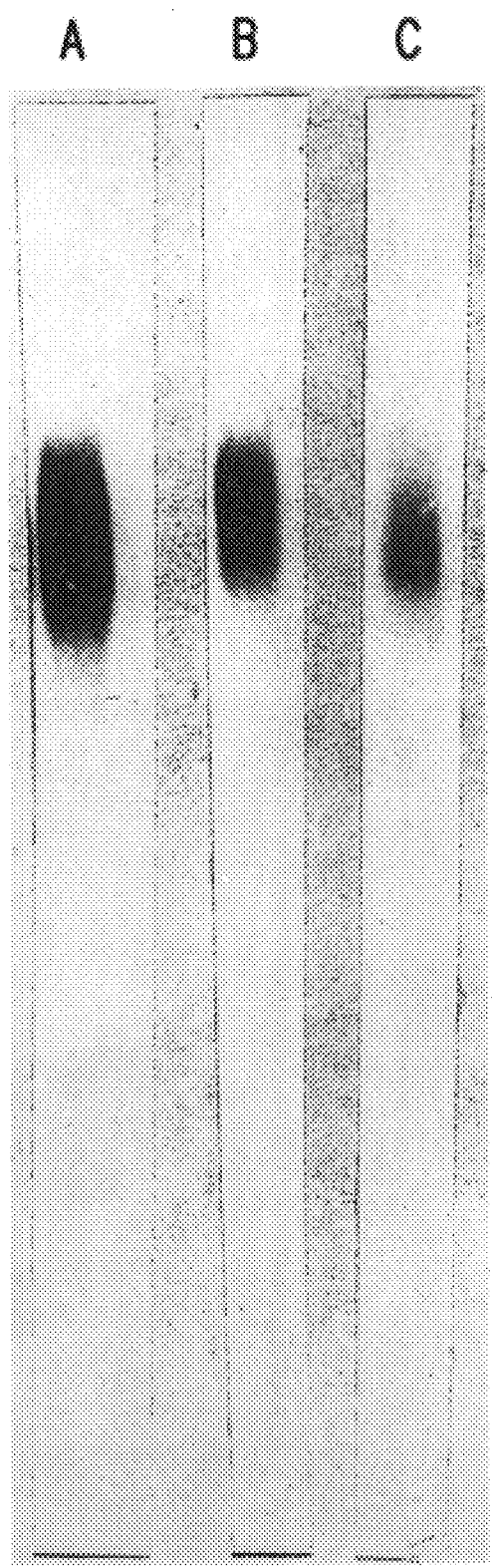
FIG. 4: a denaturing electrophoresis of Factor IX/pro-Factor IX from the stepwise chromatography (A: mixture of Factor IX/pro-Factor IX; B: pro-Factor IX; C: Factor IX).

FIG. 3 shows the chromatography profile obtained according to Example 2. Thereby it was established that Factor IX-antigen could be measured in elution buffer A (elution volume 100 ml to 110 ml) as well as in elution buffer B (elution volume 111 ml to 125 ml). However, clotting tests of the elution fractions established that physiologically active Factor IX was only found in elution buffer B (Table 2). The examination by means of denaturing electrophoresis (U. K. Laemmli, loc.cit.) established that the Factor IX-antigen of elution buffer A has a higher molecular weight by about 2000 than the active Factor IX of elution buffer B (FIG. 4).

TABLE 2

Separation of pro-Factor IX from Factor IX by Stepwise anion exchange chromatography

| Material | Volume (ml) | F IX:Ag (U) | F IX:C (U) | F IX:Ag/F IX:C |
|---|---|---|---|---|
| mixture | | | | |
| pro-F IX/F IX | 90 | 81.0 | 45.0 | 1.8 |
| Buffer A | 10 | 31.0 | 1.0 | 31.0 |
| Buffer B | 10 | 45.0 | 40.0 | 1.1 |

Example 3

Separation of Recombinant Pro-Factor IX from Recombinant Factor IX by pH Dependent Elution Materials:

Column: Mono-Q 5/5 HR, volume 1 ml (Pharmacia)

Instrument: Pharmacia FPLC LCC-500

Buffer A: 20 mM Tris/HCl buffer, pH 8.0, 150 mM NaCl

Buffer B: 20 mM Tris/HCl buffer, pH 6.0, 150 mM NaCl

A mixture of recombinant pro-Factor IX and Factor IX was produced as described in Example 1.

The ion exchange column was regenerated and equilibrated with Buffer A. Subsequently, 45 ml of the recombinant Factor IX/pro-Factor IX mixture was applied to the column with a speed of 1 ml/min. Subsequently, the column was eluted with a decreasing pH gradient from pH=8.0 to pH=6.0 by a mixture of buffer A and buffer B. Fractions of 2 ml were collected. The protein concentration was determined after the chromatography by means of the Bradford method (M. Bradford, loc.cit.). The activity of Factor IX was determined by means of a commercial coagulation test (Factor IX coagulation, Immuno AG). The concentration of Factor IX-antigen was determined by means of ELISA (Diagnostica Stago). The results established that Factor IX-antigen could be measured in the eluate at pH=7.0 to pH=7.4 as well as at pH=6.0 to 6.7.

However, further examinations of the elution fractions established that physiologically active Factor IX was only obtained in the elution fractions at pH =6.0 to 6.7. The measured values of the separation of pro-Factor IX from Factor IX are compiled in Table 3.

TABLE 3

Separation of pro-Factor IX from Factor IX by pH dependent anion exchange chromatography

| Material | Volume (ml) | F IX:Ag (U) | F IX:C (U) | F IX:Ag/F IX:C |
|---|---|---|---|---|
| mixture | | | | |
| pro-F IX/F IX | 45 | 65 | 40 | 1.6 |
| Eluate pH 7.0–7.4 | 10 | 28 | 4 | 7.0 |
| Eluate pH 6.0–6.7 | 12 | 33 | 30 | 1.1 |

Example 4

Separation of Recombinant Pro-Factor IX from Recombinant Factor IX by Immunoaffinity Chromatography Materials:

Column: anti-prosequence-Factor IX-Sepharose, volume 3 ml

Instrument: Pharmacia FPLC LCC-500

Buffer A: 20 mM Tris/HCl buffer, pH 7.4

Buffer B: 20 mM Tris/HCl buffer, pH 7.4, 3M KSCN

A mixture of recombinant pro-Factor IX and Factor IX was produced as described in Example 1.

By immunization of a goat with purified pro-peptide, antiserum was isolated which binds pro-Factor IX. This polyclonal antibody was coupled to cyanogen bromide activated Sepharose according to the manufacturer's instructions (Pharmacia). A glass column was filled with the immunoaffinity gel and equilibrated with buffer A. Subsequently, 33 ml of the mixture of recombinant Factor IX and pro-Factor IX were applied to the column with a speed of 1 ml/min. Subsequently, the column was washed with 5 ml of buffer A. Protein bound to the column was then eluted by elution with buffer B. Fractions of 2 ml were collected.

The protein concentration was determined after the chromatography by means of the method according to Bradford (loc.cit.). The concentration of Factor IX-antigen was determined by means of ELISA (Diagnostica Stago). The activity of Factor IX was ascertained by means of a commercial coagulation test (Factor IX coagulation, Immuno AG).

The determination established that Factor IX-antigen could be measured in the unbound eluate, i.e. buffer A, as well as in buffer B. However, further examinations of the elution fractions established that physiologically active Factor IX was only obtained in the unbound fraction (buffer A). Pro-Factor IX was bound by the antibody to the column and first eluted by increasing the salt concentration with buffer B. Table 4 compiles the results of the separation of pro-Factor IX from Factor IX.

TABLE 4

Separation of pro-Factor IX from Factor IX by immunoaffinity chromatography

| Material | Volume (ml) | F IX:Ag (U) | F IX:C (U) | F IX:Ag/F IX:C |
|---|---|---|---|---|
| mixture | | | | |
| pro-F IX/F IX | 33 | 150 | 90 | 1.6 |
| Buffer A | 35 | 91 | 80 | 1.1 |
| Buffer B | 10 | 50 | 3 | 17.0 |

It is to be understood that the description, specific examples and data, while indicating preferred embodiments, are given by way of illustration and exemplification and are not intended to limit the present invention. Various changes and modifications within the present invention will become apparent to the skilled artisan from the discussion and disclosure contained herein.

We claim:

1. A method for separating pro-Factor IX and Factor IX, consisting essentially of contacting a mixture of pro-Factor IX and Factor IX with an anion exchanger, and sequentially eluting with an elution buffer pro-Factor IX and Factor IX by altering the pH in the elution buffer, wherein in Factor IX after the eluting is free of pro-Factor IX and is at least 95% pure.

2. The method according to claim 1, wherein pro-Factor IX and Factor IX are separated by a decreasing pH gradient.

3. The method according to claim 1, wherein pro-Factor IX is eluted at a higher pH than Factor IX.

4. The method according to claim 1, wherein Factor IX is eluted at a pH below 7.

5. The method according to claim 4, wherein Factor IX is eluted at a pH between 5.0 to 6.9.

6. The method according to claim 1, wherein pro-Factor IX is eluted at a pH above 7.

7. The method according to claim 6, wherein pro-Factor IX is eluted at a pH between 7.0 and 8.0.

8. The method according to claim 1, wherein the Factor IX and pro-Factor IX are recombinantly produced.

* * * * *